(12) United States Patent
Archer

(10) Patent No.: US 8,557,307 B2
(45) Date of Patent: Oct. 15, 2013

(54) **METHODS AND PRODUCTS USING GRASS OF THE GENUS *TRIODIA***

(76) Inventor: Michael Archer, New South Wales (AU)

( * ) Notice: Subject to any disclaimer, the term of this patent is extended or adjusted under 35 U.S.C. 154(b) by 0 days.

(21) Appl. No.: 13/497,799

(22) PCT Filed: Sep. 21, 2010

(86) PCT No.: PCT/AU2010/001230
§ 371 (c)(1),
(2), (4) Date: Mar. 23, 2012

(87) PCT Pub. No.: WO2011/035368
PCT Pub. Date: Mar. 31, 2011

(65) Prior Publication Data
US 2012/0201913 A1    Aug. 9, 2012

(30) Foreign Application Priority Data
Sep. 23, 2009 (AU) ................... 2009904609

(51) Int. Cl.
*A01N 65/00* (2009.01)
(52) U.S. Cl.
USPC ........................................ 424/725
(58) Field of Classification Search
None
See application file for complete search history.

(56) References Cited

U.S. PATENT DOCUMENTS

| 6,767,375 | B1 | 7/2004 | Pearson |
| 2008/0102502 | A1 | 5/2008 | Foody et al. |
| 2008/0149896 | A1 | 6/2008 | Lenglet |
| 2009/0126433 | A1 | 5/2009 | Piskorz et al. |

FOREIGN PATENT DOCUMENTS

| EP | 1857532 A1 | 11/2007 |
| WO | WO2005005786 A1 | 1/2005 |
| WO | WO2008110851 A2 | 9/2008 |

OTHER PUBLICATIONS

Burrows et al., Fuel Dynamics and Fire Behaviour in Spinifex Grasslands of the Western Desert, Bushfire Conference 2006, Paper No. XXX, Brisbane, AU, Jun. 6-9, 2006.

*Primary Examiner* — Michael Meller
(74) *Attorney, Agent, or Firm* — Roger A. Jackson

(57) ABSTRACT

According to this invention, plants of the genus *Triodia* are harvested for use as a renewable energy source or as a means of carbon sequestration. *Triodia* is a hummock-forming grass endemic to Australia, commonly known as spinifex. It is an abundant perennial plant which grows in semi-arid and arid regions. The novel use of *Triodia* as a biofuel feedstock has many advantages over the prior art. Being perennial, there is no need to plant and fertilise crops. The plants can be continuously harvested without damaging the soil. *Triodia* grows well with even small amounts of natural rainfall.

1 Claim, 4 Drawing Sheets

METHODS AND PRODUCTS USING GRASS OF THE GENUS *TRIODIA*

FIELD OF THE INVENTION

The present invention relates to methods and products using grass of the genus *Triodia* systems, for example for generating energy using the plant as a feedstock.

BACKGROUND OF THE INVENTION

Systems for using plant matter as an energy source are well known. In the simplest case, biomass can be burned to release energy.

First-generation biofuels are made from sugar, starch or vegetable oil. The basic feedstocks for the production of first generation biofuels are typically seeds or grains such as wheat, which yield starch that is fermented into bioethanol. This process is of limited value for many reasons. For example, the feedstock could otherwise be used as food, and the energy consumed in cultivating it might in some cases exceed the energy recoverable froth the biofuel produced.

Second generation biofuel processes use biomass consisting of the residual non-food parts of current crops or non food crops, such as switchgrass, jatropha, cereals that bear little grain, and also industry waste such as wood chips. In the second generation process the plant's cellulose must be broken down to release the sugar which is then fermented to produce ethanol in the same way as first generation bioethanol production. The plant's remaining lignin can be burned as a carbon-neutral fuel to produce energy.

Second generation biofuels have been criticised because of the use of large scale agriculture to provide the feedstock, possible adverse effects on land, use of fertilisers and pesticides, risks posed by genetically engineering crops, consumption of large amounts of energy for processing and so on.

Energy can also be extracted from plant matter by pyrolysis and gasification, that is, heating under controlled conditions to produce combustible synthesis gas and oil which can be burnt or used for other purposes. Pyrolysis also produces a carbon-rich residue known as bio-char, which can be used as a soil enhancer. Bio-char also sequesters carbon for long periods, potentially thousands of years, as it is an extremely stable form of carbon.

SUMMARY OF THE INVENTION

The present invention provides a system for utilising plants of the genus *Triodia* as an energy source. *Triodia* is a hummock-forming grass endemic to Australia, commonly known as *spinifex*. It is an abundant perennial plant which grows in semi-arid and arid regions.

It is an object of this invention to provide a system for supplying renewable energy which does not consume plants which would otherwise provide food.

It is also an object of this invention to provide a system for providing renewable feedstocks for production of energy which requires significantly less energy and resource input than prior art biofuel systems.

It is also an object of this invention to provide a low-carbon-output system for extracting energy from renewable feedstocks.

According to one aspect of the present invention, there is provided a system for producing energy which utilises grass of the genus *Triodia* as fuel for an external combustion engine. For example, in some embodiments of this invention *Triodia* is harvested and burned to produce steam to power a turbine which drives an electrical generator.

In another aspect, the present invention provides a biofuel process which utilises grass of the genus *Triodia* as a feedstock.

In another aspect, the present invention provides a biofuel production method comprising the steps of harvesting *Triodia* and mechanically processing it to form solid fuel suitable for burning. Examples of suitable mechanical processes include grinding, chopping, pulverising, drying, pressing, compacting, pelletising and so on. In some embodiments of the invention according to this aspect, resins present in the *Triodia* help bind fibres together when the *Triodia* is compacted. In other embodiments, finely pulverised *Triodia* mixed with air or oxygen can be used as a fuel or explosive.

In another aspect, the present invention provides a biofuel production method comprising the steps of harvesting *Triodia*, pretreatment to liberate cellulose and hemicellulose, hydrolysis of cellulose and hemicellulose, fermentation, and distillation to provide ethanol. Some embodiments of the invention further comprise the step of lignin separation. In some embodiments of the invention, the pretreatment step comprises steam explosion. In other embodiments, the pretreatment step comprises mechanical treatment. In yet other embodiments, the pretreatment step comprises chemical treatment. In other embodiments, the pretreatment step comprises a combination of different treatments.

In some embodiments of the invention, hydrolysis is catalysed by enzymes. In other embodiments hydrolysis is catalysed using an acid. In some embodiments hydrolysis is assisted by use of heat, pressure or both.

In another aspect, the present invention provides a biofuel production method comprising the steps of harvesting *Triodia*, pretreatment to liberate cellulose and hemicellulose, and conversion of cellulose and/or hemicellulose to ethanol using suitable micro-organisms. Some embodiments of the invention further comprise the step of lignin separation.

In one embodiment of the invention, the pretreatment step includes utilising an acid, for example 2% sulphuric acid at about 120° C. for about 60 minutes.

In one embodiment of the invention, the hydrolysis step is achieved using, approximately, the enzymes 2% cellulase and 4% β-glucosidase at 50° C., pH 5.0 stirred at 180 rpm for 22 hours.

In one embodiment of the invention, the fermentation step is achieved using a recombinant strain of the bacterium *Zymomonas mobilis* ZM4 (pZB5), preferably for about 40-60 hours.

According to another aspect of the invention, the energy used in processing the *Triodia* feedstock is derived at least in part from solar energy. For example, pretreatment by steam explosion can be achieved using solar energy to produce the required steam.

In yet another aspect, the present invention provides a synthesis gas (carbon monoxide and hydrogen) production method comprising the steps of harvesting *Triodia* and gasification. Gasification can for example be accomplished by steam gasification or partial pyrolysis under sub-stoichiometric, high temperature conditions.

The invention in the foregoing aspect can be further extended to produce liquid hydrocarbons such as diesel fuel from *Triodia* feedstock, for example by including the further steps of the Fischer-Tropsch process.

In yet another aspect the invention provides a bio-oil production method comprising the steps of subjecting *Triodia* to pyrolysis. Preferably, anyhydrous fast pyrolysis can be used.

In another aspect the invention provides a gas production method comprising the steps of feeding *Triodia* to termites and capturing the gas emitted by the termites. In one embodiment of the invention, the gas captured is hydrogen. In another embodiment the gas captured is methane.

In yet another aspect the invention provides a gas production method comprising the steps of subjecting *Triodia* to termite gut protists and capturing the gas emitted by the protists. In one embodiment of the invention, the gas captured is hydrogen. In another embodiment the gas captured is methane.

In another aspect, the invention provides a system for obtaining volatile chemicals from *Triodia* comprising the steps of heating all or part of a *Triodia* plant and collecting volatile chemicals exuded. In some cases, material exuded sets to hard lumps after cooling and can be mechanically separated from the plant. It has been found by experiment that, for example, heating to approximately 100° C. useful organic polymers are exuded from certain species of *Triodia*. It has been found that such polymers in some cases are similar to Sandrac, Rosin and Copal. Accordingly, the present invention provides a method of using *Triodia* as a source of furniture polish, for example as an alternative to shellac or Tung oil, for the manufacture of incense, aromatic enhancers, or for medicinal uses.

In a further extension of the inventive concept, chemical exudates are fractionated to produce a range of volatile substances that have uses as biopharmaceuticals, bactericides, fungicides, insecticides, antibiotics, aromatic enhancers and so on. For example, very few animals eat *Triodia* in the wild other than termites due in part to chemicals in *Triodia* that act as deterrents to herbivory.

In yet another aspect, the present invention provides an ethanol production method comprising the steps of gasification of *Triodia*, fermentation and distillation. Fermentation can be achieved, for example, by use of suitable microorganisms such as *Clostridium ljungdahlii* bacteria which ingest the products of gasification and produce ethanol and water.

In yet another aspect, the present invention provides an ethanol production method in which the cellulose of *Triodia* is converted directly into ethanol using suitable bacteria, for example *Clostridium thermocellum*.

In yet another aspect, the invention further comprises the step of separating any resin which may be present, depending on the species of *Triodia*. For example, some species of *Triodia* have a high resin content and in an embodiment of the invention in which *Triodia* is pressed into pellets for fuel, the invention can include the step of separating the resin so that the amount of resin in the pellets is minimised. The separated resin can of course be used for other purposes.

According to another aspect of the invention, the energy used in processing the *Triodia* feedstock is derived at least in part from the products of the process, for example by burning the extracted lignin or the produced gas or ethanol.

In another aspect the invention provides a system for harvesting elements such as metals comprising the steps of harvesting *Triodia* and processing it to extract the desired elements or metals.

In yet another aspect, the invention provides a method of creating bio-char from *Triodia*. In some embodiments of this aspect of the invention, *Triodia* is subjected to pyrolysis. In other embodiments of this aspect of the invention, *Triodia* is subjected to gasification. Heating for pyrolysis or gasification can be accomplished by any of the well-known methods including solar heating, either directly or via a medium such as steam or fluid.

In yet another aspect, the invention provides a method of carbon sequestration comprising the steps of creating bio-char from *Triodia* and storing it. In some embodiments of this aspect of the invention, the storage step comprises burying the bio-char underground. In other embodiments, bio-char is simply stockpiled; for example entire valleys can be filled, providing enormous carbon sinks. In yet other embodiments the bio-char is mixed with soil. Studies have shown that addition of bio-char to soil has many benefits, including carbon sequestration, water retention, crop enhancement and so on.

The invention also consists in combinations of the foregoing aspects, for example systems which convert *Triodia* into both bio-char and ethanol or other bio-fuel.

The invention can be further adapted to improve energy efficiency by use of solar energy as the energy source for endothermic reactions of the inventive process.

In another aspect, the invention provides a method of maximising the storage of carbon in the soil in which *Triodia* grows using harvesting techniques which maximise survival of the basal clump of the plants. According to this aspect minimum damage is done to the plant's root system so that its ability to transfer carbon to the soil is maximised.

The inventive concept can also be applied to conversion of *Triodia* to animal fodder, optionally in addition to fuel. For example, in one embodiment of the invention, *Triodia* is pelletised and used as animal feed. In other variations of this inventive concept, other substances are added to the *Triodia* to improve its digestibility, palatability, nutritional value and so on as required by particular animals to be fed.

In another aspect, the invention provides a system of producing fodder comprising the steps of harvesting *Triodia* and mechanically processing it to render it edible. For example, the processing step can comprise the step of removing sharp points of the *Triodia* leaves.

The invention also consists in apparatus adapted to perform the steps of the invention described herein.

DESCRIPTION OF PREFERRED EMBODIMENTS

Embodiments of the invention will now be described with reference to the drawings in which.

Figure 1:
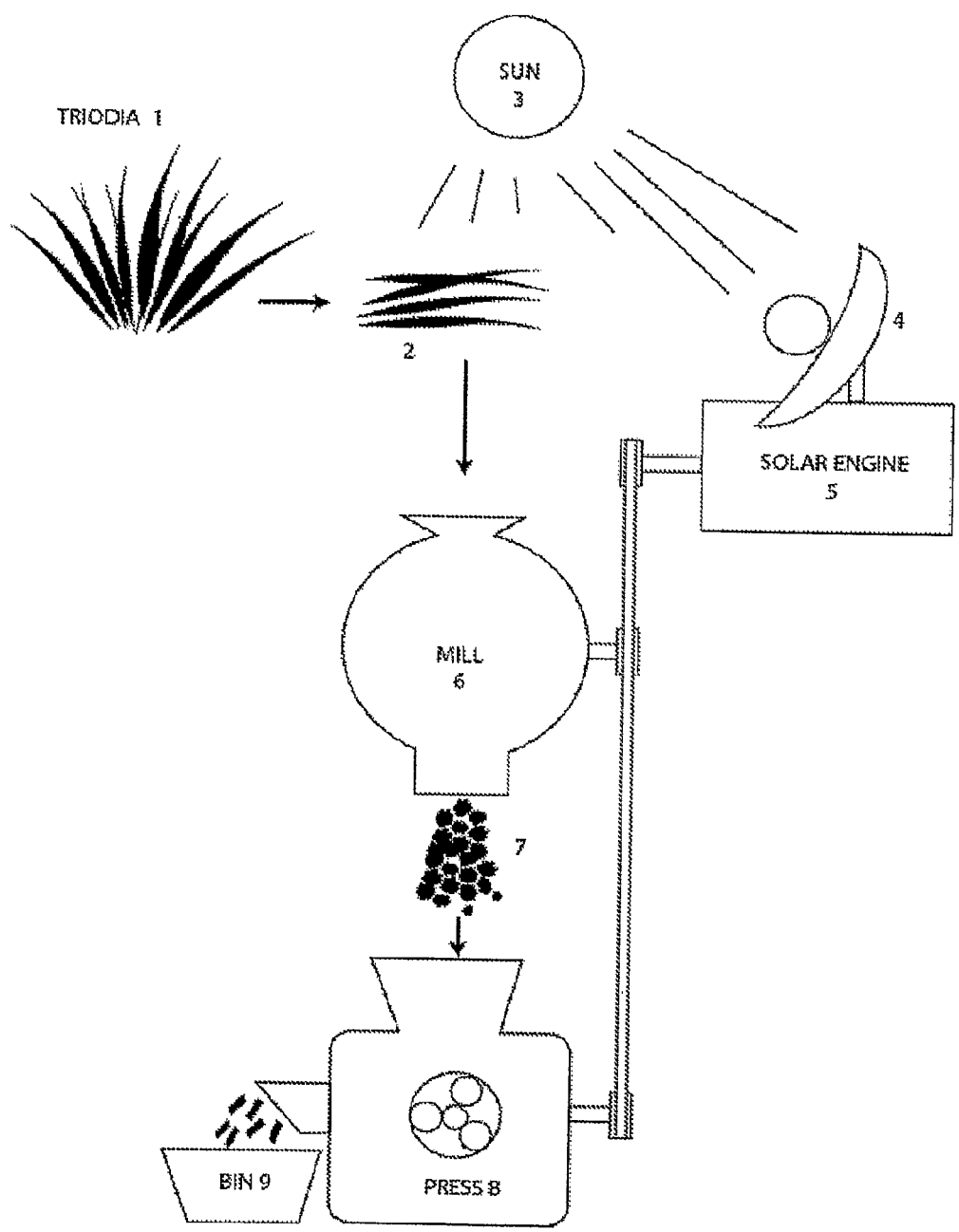
FIG. 1 is a block diagram of an embodiment of the present invention in which *Triodia* is converted into fuel pellets.

Referring now to FIG. 1, *Triodia* plants (1) are first harvested and dried (2). In this embodiment solar energy is used for drying, to maximise the carbon footprint of the process, although any other method can be used with good results. Moisture content is typically reduced to 10%-15%.

Solar energy is also collected by collector (4) which is used to power solar engine (5), which can, for example, be an external-combustion Stirling engine or a boiler/steam turbine combination. Solar engine (5) provides motive power for the other components of the system through suitable mechanical couplings.

The dried *Triodia* enters mill (6) which reduces the grass to small particles, for example 3 mm or less. The milled product (7) then passes to press (8) which is typically a ring die pellet press, which squeezes the milled product (7) through small openings, typically 4-8 mm, in a die. The pressure causes the temperature of the lignin content of the *Triodia* to rise to the degree that it plasticises slightly. The pellets are ejected from press (8) into bin (9) and when they cool, the plasticised lignin binds the particles of the pellet. In some embodiments of the invention apparatus is also provided to manage the cooling of the pellets.

Figure 2:
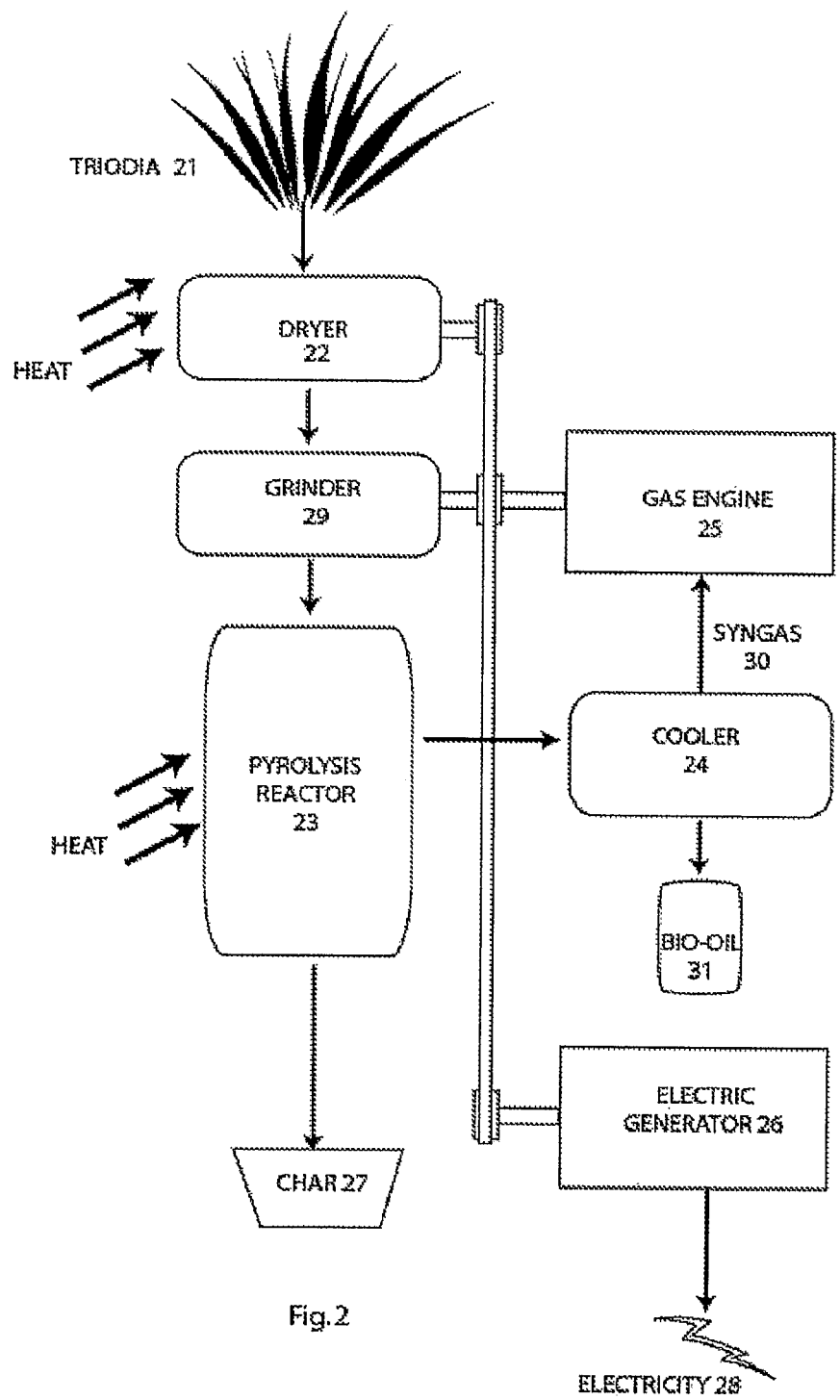
FIG. 2 is a block diagram of an embodiment of the present invention in which *Triodia* is used to generate electricity and bio-oil.

FIG. 2 illustrates the process of converting *Triodia* into char (also known as biochar), bio-oil and electricity, using pyrolysis.

*Triodia* (21) is harvested and fed into dryer (22), which is typically a tumbler which can be heated by concentrated solar energy, by burning the products of the invention or a combination of sources.

Grinder (29) chops or grinds the *Triodia* to smaller particles, facilitating the subsequent process. Pyrolysis reactor (23) heats the *Triodia* particles in the absence of oxygen. Char collected (27) can be used as a soil improver, fuel, or for carbon sequestration. Other fluid products are fed from pyrolysis reactor 23 to cooler 24, where bio-oil (31) is condensed and separated from synthesis gas (30)

The relative amounts of char, oil and gas produced by pyrolysis reactor (23) can be controlled by the conditions within the reactor. To achieve the objective of maximum energy yield for minimum carbon release, the process can be optimised to maximise the char residue.

Representative yields resulting from different parameters are summarised in the following table (Source: Aston University Bio-Energy Research Group, RenuResin Kick-off meeting, 27-28 Jan. 2003):

| Process | Liquid (bio-oil) | Solid (biochar) | Gas (syngas) |
|---|---|---|---|
| FAST PYROLYSIS Moderate temperature (~500° C.) Short hot vapour residence time (<2 s) | 75% (25% water) | 12% | 13% |
| INTERMEDIATE PYROLYSIS Low-moderate temperature, Moderate hot vapour residence time | 50% (50% water) | 25% | 25% |
| SLOW PYROLYSIS Low-moderate temperature, Long residence time | 30% (70% water) | 35% | 35% |
| GASIFICATION high temperature (>800° C.) Long vapour residence time | 5% tar (5% water) | 10% | 85% |

In this embodiment of the invention, syngas (30) is used to power gas engine (25) which provides the motive power for the processing plant. This engine also drives electric generator (25) which can be used as a source of electricity for the plant or elsewhere.

Bio-oil (31) is collected and can be used for purposes such as heating. Some of the syngas or bio-oil can be used to provide the process heat required. Solar energy can also be used for process heating.

Figure 3:
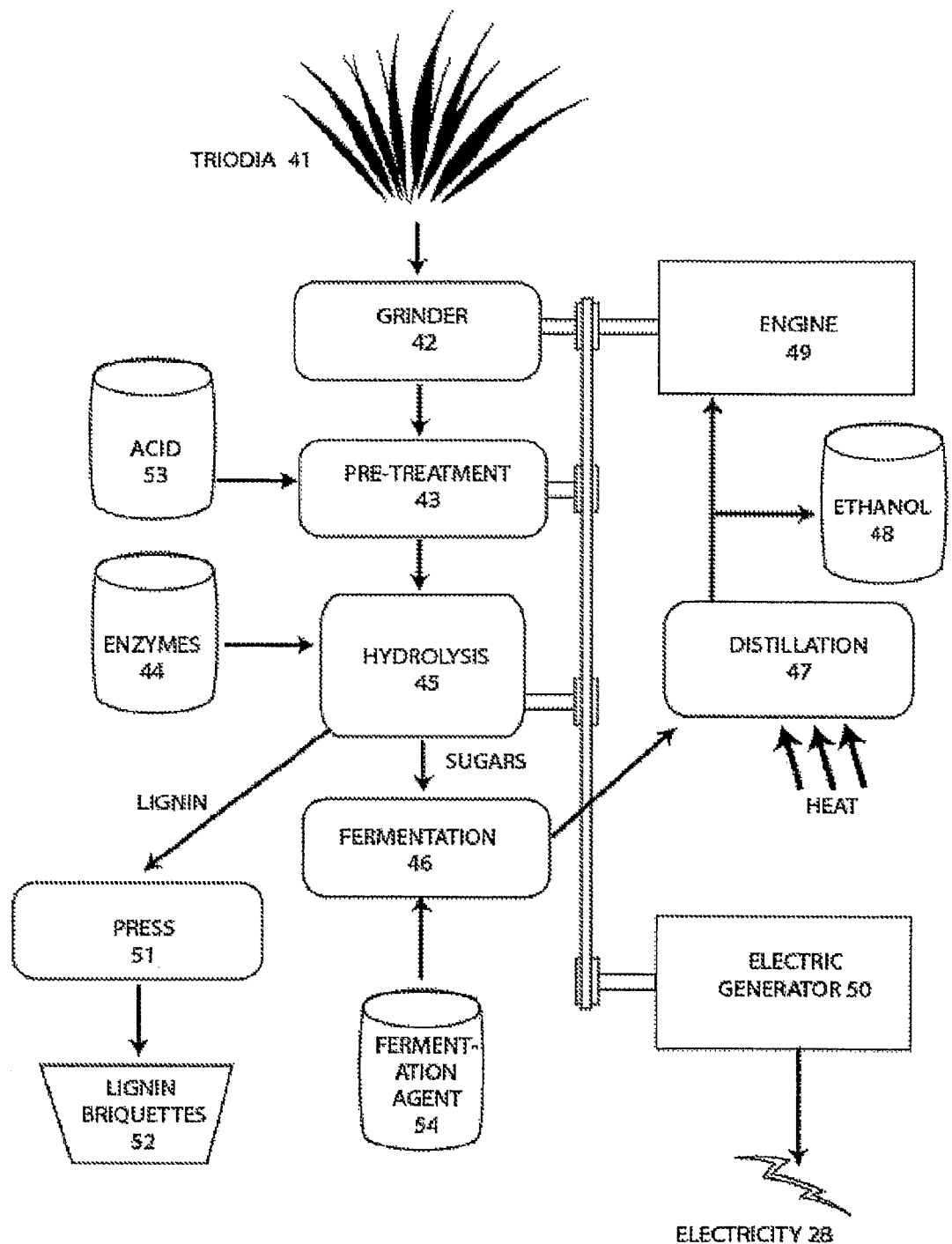
FIG. 3 is a block diagram of an embodiment of the present invention in which *Triodia* is used to generate electricity, ethanol and lignin briquettes.

FIG. 3 illustrates the process of converting *Triodia* into ethanol, electricity and solid fuel (lignin briquettes). In this embodiment, *Triodia* (41) is chopped or ground by grinder (42), which may for example comprise a hammer mill. The ground *Triodia* is then subjected to pre-treatment (43) which liberates the cellulose and hemicellulose from the plant matter. In the embodiment of the invention of FIG. 3, pre-treatment (43) comprises sugar extraction using, approximately, 2% sulphuric acid at 120° C. for 60 minutes.

The pre-treated product is then subjected to hydrolysis (45) where enzymes (44) are used to break the cellulose and the hemi-cellulose down (hydrolysed) into sugars.

Lignin is separated from the hydrolysate and after pressing (51) is collected by lignin briquette bin (52). The sugars of the hydrolysate undergo fermentation (46) through the action of fermentation agent (54).

Effective practise of hydrolysis (45) in this embodiment of the invention has been achieved using the enzymes 2% cellulase and 4% β-glucosidase at 50° C., pH 5.0 and 180 rpm for about 22 hours.

This embodiment of the invention has experimentally been found to produce 70-85% sugar recovery from *Triodia*.

Effective fermentation in this embodiment of the invention has been achieved using for the fermentation agent (54) a recombinant strain of the bacterium *Zymomonas mobilis* ZM4 (pZB5) for 40-60 hours. *Zymomonas mobilis* degrades sugars to pyruvate using the Entner-Doudoroff pathway. The pyruvate is then fermentated to produce ethanol and carbon dioxide as the only products.

The water/ethanol fermentation product is separated by fractional distillation (47). Some of the resulting ethanol is used to fuel engine (49), which provides the motive power for the processing plant, and the remainder is taken off as ethanol (48) for use as a fuel additive or other purpose.

Heat required by the process (for example distillation) is preferably provided by solar power, but can of course be provided by burning some of the produced ethanol or lignin.

This embodiment of the invention has experimentally been found to yield about 17-21 g/L ethanol, showing that the *Triodia* hydrolysate is attractive for biofuel production.

Figure 4:
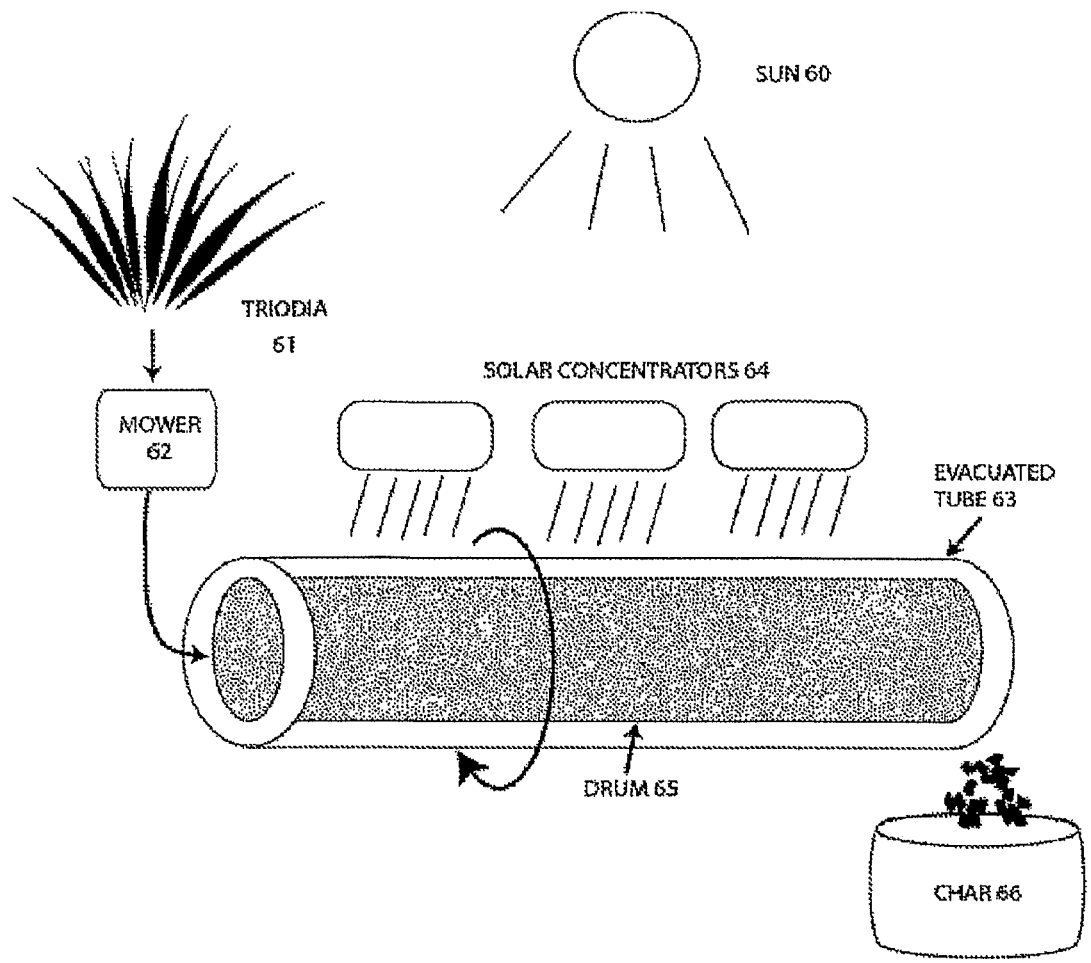
FIG. 4 is a block diagram of an embodiment of the present invention in which *Triodia* is used to create bio-char.

FIG. 4 is a block diagram of an embodiment of the present invention in which *Triodia* is used to create bio-char, which has many uses for example as a solid fuel, to improve soil quality, or for carbon sequestration etc.

The system of FIG. 4 is designed to be simple and require minimal external energy or material inputs. In this embodiment, *Triodia* (61) is mowed and the resulting chopped plant matter is fed into one end of a long drum (65). The drum is metallic and designed for maximum solar energy absorption, for example a steel drum with a dull black finish. Drum (65) is fixed inside evacuated tube (63) which is partly or completely transparent. The space between drum (65) and evacuated tube (63) is, as far as practical, evacuated so that heat conduction from drum (65) to the environment is minimised. Energy from the sun (60) is focussed on drum (65) by solar concentrators (64) resulting in heating. Drum (65) and evacuated tube (63) are rotated by suitable means, preferably solar powered.

Drum (65) performs as a pyrolysis kiln, and is accordingly adapted using well-known techniques to minimise oxygen entry and to cause the contents to travel from the entry end to the exit end. In this embodiment of the invention, chopped *Triodia* from mower (62) enters drum (65) from one end and is tumbled and heated to about 400-500° C. and travels slowly along the length of drum (65) before exiting, typically many hours later, as char into char receptacle (66).

This embodiment of the invention can be further extended to include means for capturing gas or liquid pyrolysis products which can be utilised in well-known ways.

Whereas some exemplary embodiments of the invention are described above, it will be understood that many variations can be made without departing from the scope of the invention.

For example, the harvesting of *Triodia*, referred to herein as a step of the inventive process, can include any method of removing *Triodia* from its growing environment. In most cases it is preferable that damage to the plant be minimised so that the leaves can regrow easily, to which end suitable mowing and gathering equipment can be applied. It will also be understood that it will be preferable in many cases that not all *Triodia* in a given area be removed, to minimise environmental damage and to maintain sufficient habitat for fauna. It is also environmentally beneficial to harvest the *Triodia* using a pattern which maintains firebreaks. For example, breaks 50 metres wide every 500 metres help limit the extent of fire in the event of man-made or natural fire.

It is also desirable for sustainability that the amount of *Triodia* harvested be controlled so that it is not removed faster than it can regrow. For example, in a region where *Triodia* typically takes 5 years to reach maturity, harvesting 20% of the population per annum will result in resource sustainability. The harvesting strategy can achieve both fire control and sustainability, for example by harvesting in a chequerboard pattern, harvesting say 50 metre strips perpendicularly every 250 metres.

The invention claimed is:

1. A method of producing ethanol consisting essentially of harvesting *Triodia* grass and processing said *Triodia* grass with beta-glucosidase to produce ethanol.

* * * * *